United States Patent
Kuhlmann et al.

(10) Patent No.: US 7,130,036 B1
(45) Date of Patent: Oct. 31, 2006

(54) METHODS AND SYSTEMS FOR INSPECTION OF AN ENTIRE WAFER SURFACE USING MULTIPLE DETECTION CHANNELS

(75) Inventors: Lionel Kuhlmann, San Jose, CA (US); Wayne McMillan, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 427 days.

(21) Appl. No.: 10/663,603

(22) Filed: Sep. 16, 2003

(51) Int. Cl.
*G01N 21/88* (2006.01)

(52) U.S. Cl. .................................................. 356/237.2

(58) Field of Classification Search ... 356/237.2–237.5
See application file for complete search history.

(56) References Cited

U.S. PATENT DOCUMENTS

| | | |
|---|---|---|
| 4,632,546 A | 12/1986 | Sick et al. |
| 5,274,434 A * | 12/1993 | Morioka et al. ......... 356/237.4 |
| 5,355,212 A | 10/1994 | Wells et al. |
| 5,585,916 A | 12/1996 | Miura et al. |
| 5,604,585 A | 2/1997 | Johnson et al. |
| 5,623,340 A | 4/1997 | Yamamoto et al. |
| 5,801,824 A | 9/1998 | Henley |
| 5,999,266 A | 12/1999 | Takahashi et al. |
| 6,020,957 A * | 2/2000 | Rosengaus et al. ...... 356/237.4 |
| 6,034,776 A | 3/2000 | Germer et al. |
| 6,204,917 B1 | 3/2001 | Smedt |
| 6,271,916 B1 | 8/2001 | Marxer et al. |
| 6,356,346 B1 | 3/2002 | Hagen et al. |
| 6,407,809 B1 | 6/2002 | Finarov et al. |
| 6,496,256 B1 | 12/2002 | Eytan et al. |
| 6,507,394 B1 | 1/2003 | Cheng et al. |
| 6,509,965 B1 | 1/2003 | Fossey et al. |
| 6,515,742 B1 | 2/2003 | Ruprecht |
| 6,201,601 B1 | 3/2003 | Vaez-Iravani et al. |
| 6,538,730 B1 | 3/2003 | Vaez-Iravani et al. |
| 6,559,938 B1 | 5/2003 | Smedt |
| 6,608,676 B1 * | 8/2003 | Zhao et al. .............. 356/237.2 |
| 2001/0028454 A1 | 10/2001 | Savareigo |
| 2002/0145732 A1 | 10/2002 | Vaez-Iravani et al. |
| 2002/0149765 A1 | 10/2002 | Fujii et al. |
| 2003/0030050 A1 | 2/2003 | Choi |
| 2003/0030795 A1 | 2/2003 | Swan et al. |

FOREIGN PATENT DOCUMENTS

| | | |
|---|---|---|
| JP | 9-191037 | 7/1997 |
| WO | 97/39339 | 10/1997 |

\* cited by examiner

*Primary Examiner*—Richard A. Rosenberger
(74) *Attorney, Agent, or Firm*—Ann Marie Mewherter; Daffer McDaniel, LLP

(57) ABSTRACT

Methods for inspecting a wafer are provided. One method includes directing light to a center portion and an edge portion of a wafer in a single scan. The method also includes detecting light scattered from the center portion using a first detection channel and detecting light scattered from the edge portion using a second detection channel. Another method for inspecting an edge portion of a wafer includes scanning the edge portion of the wafer with light. The method also includes separately detecting different portions of light scattered from the edge portion. In addition, the method includes separating light scattered from edge features in the edge portion from other light scattered from the edge portion. The method further includes detecting defects in the edge portion of the wafer using the other scattered light.

19 Claims, 4 Drawing Sheets

METHODS AND SYSTEMS FOR INSPECTION OF AN ENTIRE WAFER SURFACE USING MULTIPLE DETECTION CHANNELS

BACKGROUND OF THE INVENTION

1. Field of the Invention

The present invention generally relates to methods and systems for inspection of an entire wafer surface using multiple channels. Certain embodiments relate to detecting light scattered from different portions of the entire wafer surface using different detection channels.

2. Description of the Related Art

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Wafers may contain defects both in central portions of the wafers as well as in edge portions of the wafers, which includes a relatively narrow region around the periphery of the wafers, and on the outer edge of the wafers. Examples of defects that may be found in the edge portion and on the outer edge of wafers include, but are not limited to, chips, cracks, scratches, marks, particles, and residual chemicals (e.g., resist and slurry). As wafer sizes continue to increase, both wafer and integrated circuit (IC) manufacturers are becoming more concerned about defectivity at or near the wafer edge. The main concerns are that edge defects could fall onto the central part of the wafer thereby causing untraceable yield loss, cross contamination during processing, and/or catastrophic wafer breakage. These yield loss mechanisms are experienced by most wafer and IC manufacturers at one time or another.

Traditionally, wafer inspection tools are designed to inspect a central portion of the wafers (i.e., a surface area of the wafer on which electrical elements will be formed or a surface area of the wafer opposite that on which electrical elements will be formed). Since these areas of the wafer reflect or scatter relatively small amounts of light, such wafer inspection tools are designed to detect relatively small amounts of light. However, near the outer edge of the wafer, relatively large amounts of light may be reflected or scattered from the wafer due to edge features such as a bevel formed at or near the outer edge. As a result, these large amounts of light will saturate the detectors of traditional wafer inspection systems. Consequently, any output signals generated near or at the edge of wafers by such wafer inspection tools are generally unusable. In some instances, the wafer inspection systems may be designed to block the light from reaching the detectors when inspecting near the edge of the wafer to protect the detectors from damage that may be caused by the relatively high intensity light.

Some edge inspection systems are being developed to detect defects at or near the outer edge of wafers. Examples of apparatuses for detecting defects along the edge of electronic media such as semiconductor wafers are illustrated in U.S. Patent Application Publication Nos. 2003/0030050 by Choi and 2003/0030795 by Swan et al., which are incorporated by reference as if fully set forth herein. Due to the substantially different reflecting and scattering characteristics of the outer edge of wafers in comparison to the inner portion of the wafer, such edge inspection systems have substantially different configurations than the traditional wafer inspection tools. Therefore, the edge inspection systems are not optimized to, or even able to, detect defects in the central portion of the wafers. Consequently, if wafer or IC manufacturers want to detect defects in both the central and outer portions of wafer (as is usually the case since defects in either portion may result in expensive yield losses and other problems), they will need to purchase two separate tools. Using two different wafer inspection tools instead of just one inspection tool will obviously increase costs in many ways such as increases in clean room real estate and operating costs, increases in tool maintenance costs, and increases due to reduced throughput. However, since a tool that is capable of inspecting both the inner and outer portions of wafers is not currently available, and due to the increasing costs associated with defect-based yield losses, wafer and IC manufacturers may not be able to avoid the costs associated with multiple, different inspection tools.

Accordingly, it may be advantageous to develop a wafer inspection system that is capable of inspecting substantially an entire surface of wafers including both center and edge portions of the wafers.

SUMMARY OF THE INVENTION

An embodiment of the invention relates to a method for inspecting a wafer. The method includes directing light to a center portion and an edge portion of the wafer in a single scan. In one embodiment, the edge portion may extend about 3 mm inward from an outer edge of the wafer. In another embodiment, the center portion and the edge portion have a combined surface area approximately equal to an entire surface area of a front side of the wafer. In a different embodiment, the center portion and the edge portion have a combined surface area approximately equal to an entire surface area of a back side of the wafer.

The method also includes detecting light scattered from the center portion of the wafer using a first detection channel. In addition, the method includes detecting light scattered from the edge portion of the wafer using a second detection channel. In one embodiment, the first and second detection channels include different types of detectors. For example, the first detection channel may include a photomultiplier tube. In addition, the first detection channel may be configured to generate a single output signal at each measurement spot. In contrast, the second detection channel may include a segmented detector. In another embodiment, the second detection channel may include an array of photosensitive elements. In addition, the second detection channel may be configured to separately detect different portions of the light scattered from the edge portion. In one such embodiment, the method may also include separating light scattered from edge features of the wafer from other light scattered from the edge portion.

In another embodiment, the method may include collecting the light scattered from the center and edge portions of the wafer with a single collection channel. Such a method may also include directing the light collected by the single collection channel to the first and second detection channels. In some embodiments, the method may include collecting the light scattered from the edge portion of the wafer with a collector. In one such embodiment, the collector may provide a Fourier plane suitable for Fourier filtering of the light scattered from the edge portion. In an additional embodiment, the method may include substantially preventing the light scattered from the edge portion from reaching a detector of the first detection channel.

In one embodiment, the center and edge portions of the wafer may be located on a front side of the wafer. Such an embodiment of the method may include inspecting the front side of the wafer, substantially an entire backside of the wafer, and an outer edge of the wafer while the wafer is disposed in a single tool. The method may include any other steps of any of the methods described herein.

An additional embodiment relates to a method for inspecting an edge portion of a wafer. The method includes scanning the edge portion of the wafer with light. The edge portion extends about 3 mm inward from an outer edge of the wafer. The method also includes separately detecting different portions of light scattered from the edge portion. In addition, the method includes separating light scattered from edge features in the edge portion from other light scattered from the edge portion. The method further includes detecting defects in the edge portion of the wafer using the other scattered light. In some embodiments, the method may also include collecting the light scattered from the edge portion with a collector. The collector may provide a Fourier plane suitable for Fourier filtering of the light scattered from the edge portion. The method may include any other steps of any of the methods described herein.

Another embodiment relates to a method for inspecting a wafer. In one embodiment, the wafer may be an unpatterned wafer. The method includes directing light to substantially an entire surface of the wafer in a single scan. In an embodiment, the entire surface of the wafer may be a front side surface of the wafer. In an alternative embodiment, the entire surface of the wafer may be a back side surface of the wafer. The entire surface may include a center portion and an edge portion. The method also includes separately detecting different portions of light scattered from the wafer to generate individual output signals representative of the different portions of light. In addition, the method includes combining the individual output signals generated at the same measurement spots during detection of the different portions of light scattered from the center portion of the wafer. The method further includes detecting defects in the center portion of the wafer using the combined output signals. Additionally, the method includes detecting defects in the edge portion of the wafer using the individual output signals. The method may include any other steps of any of the methods described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
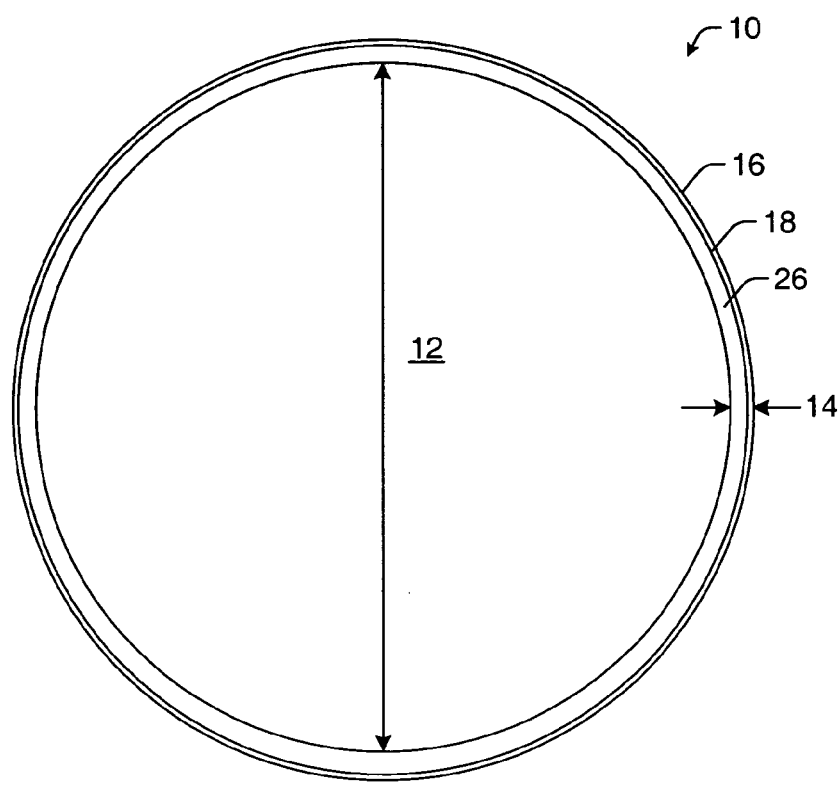
FIG. 1 is a schematic diagram illustrating a top view of a wafer.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers that may be formed upon a substrate. For example, such layers may include, but are not limited to, a resist, a dielectric material, and a conductive material. A resist may include a resist that may be patterned by an optical lithography technique, an e-beam lithography technique, or an X-ray lithography technique. Examples of a dielectric material may include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably herein with the term "integrated circuit." In addition, although some embodiments are described herein with respect to an integrated circuit, it is to be understood that these embodiments may be similarly applied to other semiconductor devices such as microelectromechanical (MEMS) devices and the like.

Turning now to the drawings, it is noted that FIGS. 1–7 are not drawn to scale. In particular, the scale of some of the elements of the figures are greatly exaggerated to emphasize characteristics of the elements. It is also noted that FIGS. 1–7 are not drawn to the same scale. Elements shown in more than one figure that may be similarly configured have been indicated using the same reference numerals.

FIG. 1 illustrates a top view of wafer 10. As shown in FIG. 1, wafer 10 includes center portion 12 and edge portion 14. Edge portion 14 is located near the periphery of the wafer and completely surrounds the center portion of the wafer. In some embodiments, edge portion 14 extends about 3 mm inward from outer edge 16 of the wafer. However, the edge portion may extend more than about 3 mm inward from the outer edge of the wafer (e.g., about 5 mm or about 6 mm). As shown in FIG. 1, the center portion and the edge portion have a combined surface area approximately equal to an entire surface area of a front side or a back side of the wafer.

Figure 2:
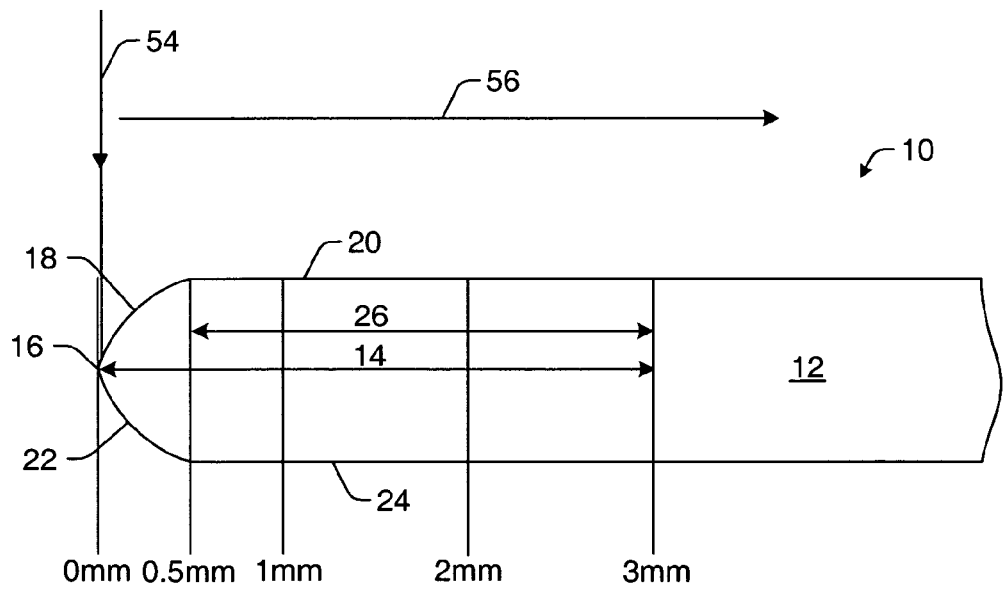
FIG. 2 is a schematic diagram illustrating a partial cross-sectional view of a wafer.

Edge portion 14 includes bevel 18, which extends from the outer edge of the wafer inward by about 0.5 mm. As shown in FIG. 2, which is a partial cross-sectional view of wafer 10, bevel 18 extends from outer edge 16 of the wafer to front side surface 20 of the wafer. As further shown in FIG. 2, a surface of bevel 18 is arranged at an angle to the front side surface of the wafer. In addition, bevel 22 extends from outer edge 16 of the wafer to back side surface 24 of the wafer. Bevel 22 may also extend from the outer edge of the wafer inward by about 0.5 mm. Bevel 18 and bevel 22 meet at the outer edge of the wafer forming an apex. Edge portion 14 also includes edge region 26 shown in FIGS. 1 and 2, which extends from bevel 18 to center portion 12 of the wafer. Edge region 26 may extend about 2.5 mm or greater inward from bevel 18. For example, the edge region may be defined as the distance from the bevel upon which semiconductor fabrication of any kind is excluded. Therefore, the extent of the edge region may vary depending upon, for example, the size of the wafer, the characteristics of the semiconductor devices or integrated circuits being formed upon the wafer, and parameters of the semiconductor fabrication process used to process the wafer.

Defects in the center portion of the wafer have been the primary concern for wafer and integrated circuit (IC) manufacturers since this is the area of the wafer upon which IC and semiconductor devices are fabricated. Therefore, many wafer inspection systems have been designed to detect defects in the center portion of the wafer. However, as described in more detail above, wafer and IC manufacturers are becoming more concerned about defects at or near the wafer edge. Since many traditional wafer inspection tools are not capable of inspecting wafers at or near the wafer edge, some wafer inspection systems have been developed for inspection of areas at or near the wafer edge. Such wafer edge inspection tools, however, are not capable of inspecting the center portion of wafers due to the configuration of these tools. As such, a wafer inspection tool that can inspect both the center and edge portions of a wafer may be particularly advantageous to reducing inspection costs and increasing throughput for inspection and thereby for wafer and IC manufacturing.

Various methods for inspecting both center and edge portions of a wafer in a single scan are described herein. The methods described herein are advantageous for many reasons. For example, one wafer inspection system can be used to inspect both the center and edge portions of a wafer in a single scan. Therefore, the inspection methods described herein may reduce the number of tools required to inspect an entire surface of a wafer thereby reducing wafer and IC manufacturers capital and operating costs. In addition, since the entire wafer surface can be inspected in one tool, wafer inspection throughput may be increased thereby increasing the overall manufacturing throughput.

Figure 3:
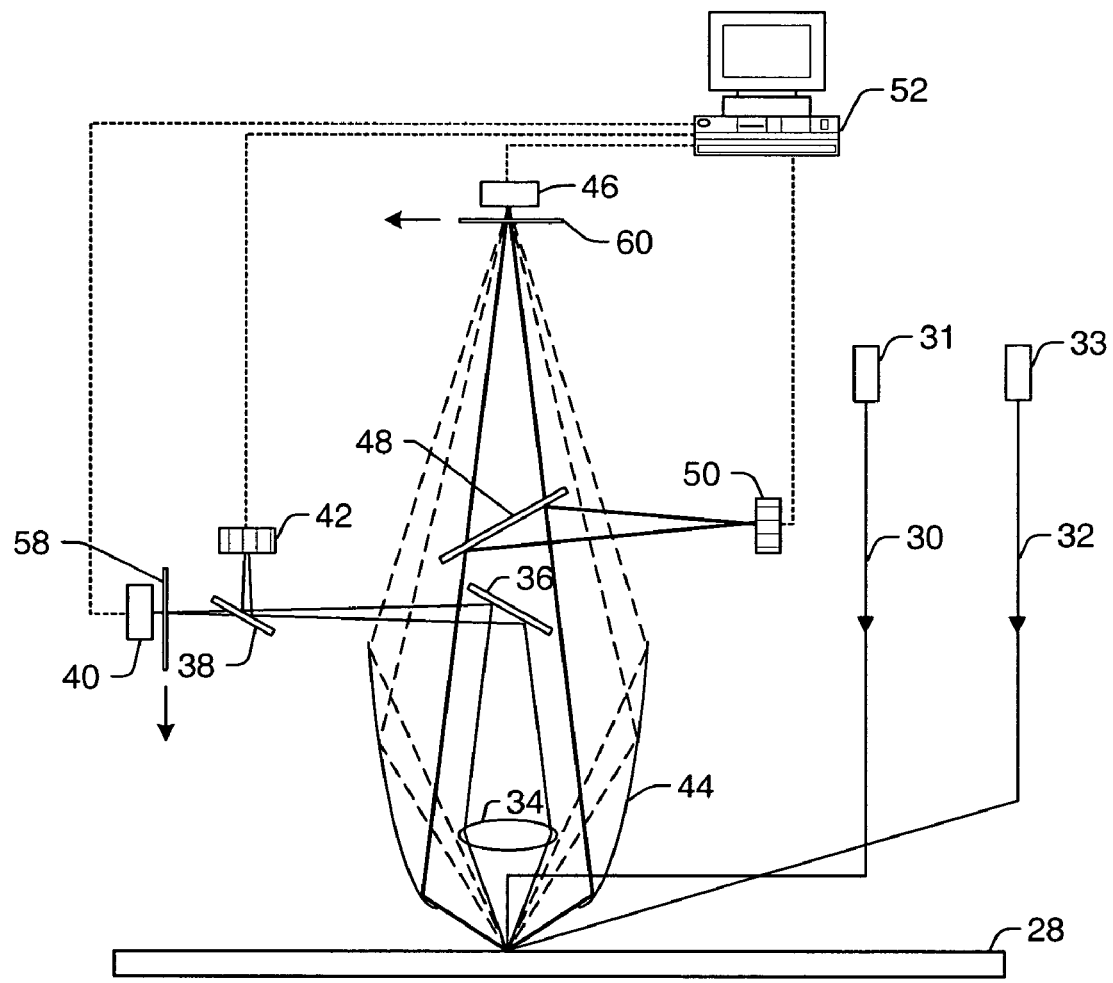
FIGS. 3–6 are schematic diagrams illustrating various embodiments of a wafer inspection system that can be used to inspect substantially an entire surface of a wafer in a single scan.

One example of a wafer inspection system that can be used to perform a method for inspecting substantially an entire surface of a wafer in a single scan is illustrated in FIG. 3. The wafer inspection system shown in FIG. 3 is an inspection tool configured for patterned and unpatterned wafer inspection and is based on the $SP^{TBI}$ system, which is commercially available from KLA-Tencor, San Jose, Calif. This wafer inspection system is described in more detail in U.S. Pat. No. 6,538,730 to Vaez-Iravani et al., which is incorporated by reference as if fully set forth herein. For the sake of clarity, some of the components and details of the system have been omitted from FIG. 3 and the corresponding description presented herein. However, it is to be understood that the system illustrated in FIG. 3 may be further configured as described in this patent. In addition, U.S. Pat. No. 6,538,730 is related to U.S. Pat. No. 6,201,601 to Vaez-Iravani et al. and U.S. Pat. No. 6,271,916 to Marxer et al., which are also incorporated by reference as if fully set forth herein. The wafer inspection system described herein may be further configured as described in these patents.

Wafer 28 to be inspected is illuminated by normal incidence beam 30 and/or oblique incidence beam 32, which may be generated by light sources 31 and 33, respectively. The light sources may include any suitable light sources known in the art. The system may also include a number of optical components such as folding mirrors (that are not shown in FIG. 3 for simplicity) to direct the beams to the surface of the wafer as shown in FIG. 3. Wafer 28 is supported on a chuck (not shown), which may be rotated and translated such that beams 30 and/or 32 illuminate an area or spot on the wafer which is caused to move in a spiral path on the surface of the wafer. Alternatively, beams 30 and/or 32 may be caused to move in a manner known to those skilled in the art to trace the spiral path or another type of scan path across the wafer.

The area or spot illuminated by either one or both of the beams on the wafer scatters light from the beam(s). The light scattered by the illuminated area on the wafer along directions close to perpendicular to the surface of the wafer is collected and focused by lens collector 34 and directed by mirror 36 and beamsplitter 38 to detectors 40 and 42. Since lens collector 34 collects light scattered along directions close to the normal direction, this collection channel is referred to as the narrow channel. When desired, one or more polarizers (not shown) may be placed in the path of the collected light in either or both of the detection channels. Light scattered by the spot on the wafer illuminated by either one or both of the beams along directions away from the normal direction is collected by ellipsoidal mirror 44 and may be focused through an aperture (not shown) and optional polarizers (not shown) to detector 46. In addition, beamsplitter 48 is configured to direct a portion of the light collected by ellipsoidal mirror 44 to detector 50. Since the ellipsoidal mirror collects scattered light along directions at wider angles from the normal direction than lens collector 34, this collection channel is referred to as the wide channel. Outputs of detectors 40, 42, 46, and 50 are supplied to computer 52. For example, detectors 40, 42, 46, and 50 may be coupled to computer 52 by a transmission medium as shown by the dotted lines in FIG. 3. Computer 52 may process the signals and may determine the presence of defects and their characteristics.

The collection optics of the system shown in FIG. 3 are rotationally symmetric about the normal direction. The lens collector and the ellipsoidal mirror preserve the azimuthal information contained in light scattered by defects on the surface of the wafer. Therefore, certain defects and/or patterns on the wafer may scatter light preferentially along certain azimuthal directions more than other azimuthal directions. By making use of the preserved azimuthal information in the light collected by lens 34 and mirror 44, the system is advantageously adapted and modified for the detection of defects on patterned wafers. In addition, the system is advantageously modified for detection of defects in the edge portion of patterned and unpatterned wafers.

By segmenting a portion of the light collected by the lens and/or the ellipsoidal mirror, light scattered in different azimuthal directions may be detected separately. In this manner, some segments of the detectors detecting light diffracted or scattered by a pattern may become saturated, while other segments of the detectors will yield useful signals for the detection and classification of defects on the wafer. Since the lens and the ellipsoidal mirror preserve the azimuthal information of the scattered light, knowledge of the type of pattern, features, or defects present on the wafer can be advantageously used to design and position multiple detectors to advantageously detect and classify the defects on the wafer. This is especially true in the case of regular patterns such as memory structures on the wafer since light diffracted by regular patterns also tends to be regular.

A convergent hollow cone of light may be collected by lens 34 and/or mirror 44. In the case of lens 34, a spatial filter (not shown) may be employed to block the specular reflection of the normal incidence beam from reaching detectors 40 and 42 so that the light focused by lens 34 to detectors 40 and 42 has the shape of a convergent hollow cone. In the case of the ellipsoidal mirror, since the mirror is not a complete ellipse, it collects only light scattered at larger angles to the normal direction without also collecting the light scattered at near normal directions so that the light focused by mirror 44 towards detectors 46 and 50 also has the shape of a convergent hollow cone.

An arrangement of multiple fiber channels (not shown) receiving light in the convergent cone of light such as that collected by mirror 44 may be used to direct light to one of the two detectors configured to detect light collected by the mirror (e.g., detector 50). One arrangement includes two substantially concentric rings of optical fiber channels (not shown) that are used to carry the collected scattered light in the convergent hollow cone. Another arrangement of the multiple fiber channels may include one ring of optical fiber channels (not shown) that can be used to carry the collected scattered light. Fourier components or other scattering from features on the wafer may reach some of the fibers thereby causing the detectors detecting the light from such channels to be saturated. However, there will be other optical fiber channels that do not receive such unwanted pattern or feature scattering. The use of multiple fiber channels effectively segments the collected scattered light into different sectors or segments so that only some of the fiber channels will receive a strong signal and can become saturated due to Fourier or other feature scatter leaving the remaining channels carrying information that can be analyzed for detecting anomalies. Since the azimuthal information in the collected scattered light is preserved, various schemes may be used to minimize the effects of the pattern or feature scatter when the segmented approach is used.

Different types of segmented detectors may be used to detect the light carried by the fiber channels such as a multi-anode photo-multiplier tube (PMT) or a multi-PIN diode array. In the event that a multi-anode PMT is used, however, there may be a nominal 3% cross-talk between any two adjacent channels. To avoid such cross-talk, the fibers may be aligned with every other PMT anode. This arrangement avoids the 3% cross-talk that may be present if all of the anodes are aligned with fibers. In addition, the optically transmissive cores of optical fibers that are located adjacent to each other may be separated from each other by the claddings that envelope the cores so that cross-talk between adjacent cores may be reduced. Obviously, optical channels other than fibers may be used and are within the scope of this disclosure. Where such channels do not include separators such as the claddings in the case of optical fibers, other optical separators may be used to reduce cross-talk.

As described above, beamsplitter 38 reflects and diverts a portion of the collected light from lens 34 to an arrangement of optical fibers (not shown). Preferably, the size of the optical fibers collect and convey most of the light in the hollow cone of light. Each of the fibers may be connected to a corresponding detector or a detecting unit in a multi-unit or multi-element detector. In a similar manner, beamsplitter 48 diverts a portion of the light collected by mirror 44 towards an arrangement of optical fiber channels (not shown) where each channel is connected to a separate detector or separate detecting unit in a multi-element detecting system. As shown in FIG. 3, beamsplitter 48 is configured such that it diverts light only within a narrow ring to the arrangement of optical fiber channels. Most of the light collected by mirror 44 is passed through beamsplitter 48 and focused to detector 46 to provide a single output. Therefore, the system illustrated in FIG. 3 diverts a portion of the scattered light collected by lens 34 and mirror 44 and directs this portion of the scattered light towards fibers to convey the segmented light to segmented detectors 42 and 50. In this manner, a single instrument may include different types of detection channels coupled to each collection channel; one non-segmented detection channel, which is particularly suitable for unpatterned wafer inspection, and one segmented detection channel, which is particularly suitable for patterned wafer inspection. It is also possible to place the individual detectors or multi-element detecting systems directly in the path of the converging hollow cone of light, rather than in the path of individual optical fibers.

Where the system illustrated in FIG. 3 is used for inspecting wafers with memory cells formed thereon, the Fourier components from the memory array will spin as the wafer is rotated. These components will thus rotate and be at different azimuthal angles about the normal direction. As a result, these Fourier components will be conveyed by different fibers as the wafer is rotated. Since the array of memory cells may have different dimensions in the X and Y directions of the wafer, as the wafer rotates, the number of detectors that are saturated by the Fourier components will change. By knowing the X and Y dimensions of the memory cells, the number of Fourier diffraction components can be estimated. Alternatively, during an initialization process at the beginning, a learn cycle may be performed where the maximum number of Fourier components that need to be eliminated is determined by noting the maximum number of detectors with very strong, or saturated, outputs. During the subsequent measurement, this number of detector outputs may then be eliminated, where the outputs eliminated are the ones that are saturated or the ones that have the largest values. In the case of a multi-anode PMT, for example, where each anode is used and is connected to a corresponding fiber, cross-talk may be reduced by also eliminating the components adjacent to the detectors having the highest outputs. For example, if the wafer in one position gives three Fourier components, and in another two, the three direct components together with the two components adjacent to each would be eliminated for a total of nine detector outputs that are eliminated. This leaves seven usable detector outputs. This number will be maintained regardless of the exact orientation of the wafer. This allows the user to maintain the sizing option for the particles.

Preferably, the fibers or the segmented detectors are arranged rotationally symmetrically around a direction. When arranged in such manner, the light scattering directions are partitioned into identical angular segments and light scattered within each segment is collected by a corresponding fiber. When mirror 36 and beamsplitters 38 and 48 reflect or divert a portion of the light collected by lens 34 or mirror 44, the azimuthal positions of the collected scattered light are preserved when the reflected or diverted light is directed to the fibers or the segmented detectors. Therefore, azimuthal characterizations of scattered light are preserved both for the narrow and the wide channels.

If all of the scattered light from the illuminated spot on the wafer is collected and directed to a single non-segmented detector, the presence of Fourier or other scatter components will cause the detector to saturate so that the system will not be able to provide useful information concerning anomalies in the illuminated spot. For this reason, the collected scattered light is segmented into different segments. If the collected scattered light is divided into very few segments, such as two or three, resulting in two or three output signals, the probability may be high that the two or three segments would still contain pattern scatter so that the two or three detectors would again become saturated and yield no useful information concerning defects. Thus to be useful, the segmentation is preferably fine enough that at least some of the detector signals contain no significant pattern scatter. For example, as explained in more detail in U.S. Pat. No. 6,538,730 to Vaez-Iravani et al., where the segmented light is conveyed to multiple optical fibers, it is preferable for at least some of the fibers to receive light collected within azimuthal angles of no more than $\delta\phi$.

The system illustrated in FIG. 3 is particularly advantageous for distinguishing between micro-scratches and particles as further described in U.S. Pat. No. 6,538,730 to Vaez-Iravani et al. The system illustrated in FIG. 3 may be further configured as described in this patent.

According to one embodiment, the above-described system may be used to perform a wafer inspection method that includes directing light to a center portion and an edge portion of a wafer in a single scan. Therefore, substantially an entire wafer surface may be inspected in a single scan. For example, the above-described system may be used to direct a normal incidence beam and/or an oblique incidence beam to the surface of a wafer. In addition, the normal incidence beam and/or the oblique incidence beam may be caused to trace a spiral-like path or another path across the wafer. Furthermore, as shown in FIG. 2, incident light 54 (shown generally as a normal incidence beam of light) may be scanned across the wafer from outer edge 16 across edge portion 14 and center portion 12 in a single scan.

The position of the incident light on the wafer may be monitored during the single scan. For example, the position of the incident light may be determined within respect to an alignment mark such as a notch, a flat, or some other indentation into the periphery of the wafer. In other cases, the alignment mark may be a permanent identification mark such as a series of alphanumeric characters formed on the specimen. In addition, the alignment mark may include any feature formed on the specimen. The alignment mark may be detected using one or both of the light beams prior to commencing the scanning of the wafer. Alternatively, the alignment mark may be detected using a separate alignment module (not shown), which may be coupled to the wafer inspection system. Any other method for determining the position of incident light with respect to the wafer may be used.

When the light is directed to the center portion of the wafer, the light scattered from the center portion of the wafer may be detected using a first detection channel. For example, in the case of an unpatterned wafer, the center portion of the front side of the wafer and the center portion of the back side of the wafer will not have any patterned features that would produce Fourier components or other strong scattering. Therefore, light scattered from the center portion of an unpatterned wafer will not cause a non-segmented detector to become saturated. As a result, the first detection channel may include a non-segmented detector that may be used to detect the light scattered from the center portion of an unpatterned wafer. In addition, in the case of a patterned wafer, the center portion of the back side of the wafer will not have any patterned features that would produce Fourier components or other strong scattering. Therefore, the first detection channel may be used to detect light scattered from the center portion of the back side of a patterned wafer.

The non-segmented detector may be configured to generate a single output signal at each measurement spot in the center portion of the wafer. In one embodiment, the non-segmented detector may be a highly sensitive detector like a PMT (e.g., a single-anode PMT) or another high efficiency detector. In addition, any other suitable detector known in the art may be used for the non-segmented detector. In this manner, when the system illustrated in FIG. 3 is used to perform this method, the light scattered from the center portion of the wafer may be detected using detector 40 and/or detector 46. Output signals generated by detector 40 and/or detector 46 during scanning of the center portion of the wafer may be used by computer 52 to detect defects in the center portion of the wafer. The computer may also perform a number of other operations on the output signals.

Light scattered from the center portion of the wafer may also be directed to detector 42 and/or detector 50. While the diversion of some of the collected scattered light from detectors 40 and 46 may somewhat reduce the sensitivity of these detectors, such reduction is not significant due to the high efficiency of the narrow and wide collection channels of the system. If desired, when portions of the wafer not containing patterned features or edge features are being inspected, light conveyed by the optical fibers may be directed towards the non-segmented detectors instead of the segmented detectors so that the resulting sensitivity is substantially the same as if the light was not diverted at all. In addition, even if the light directed to detector 42 and/or detector 50 is not redirected in this manner, any output signals generated in response to light detected by these detectors during scanning of the center portion of the wafer may not be used for defect detection.

Figure 7:
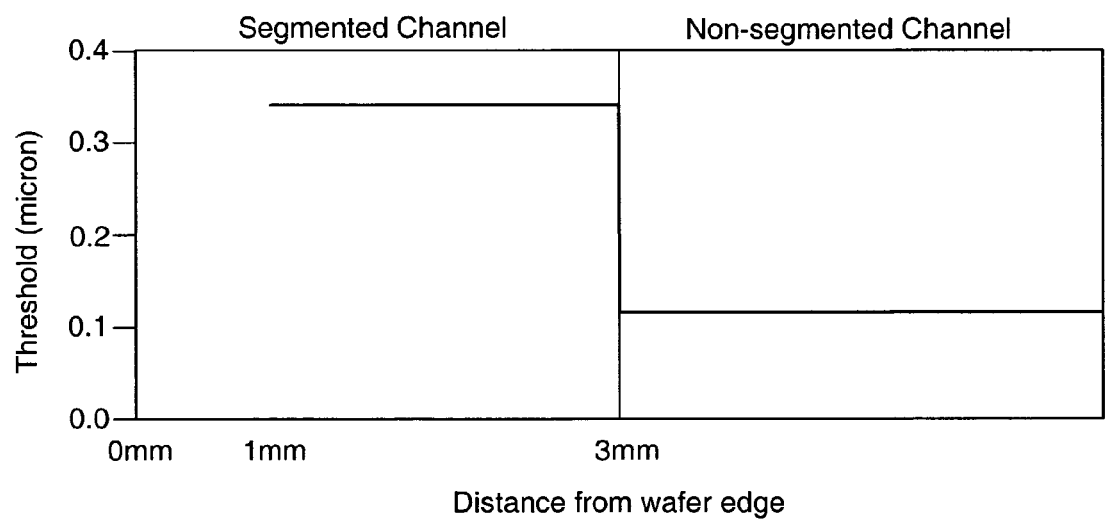
FIG. 7 is a diagram illustrating the sensitivity for defect detection at various portions of a wafer.

When the light is scanned over the edge portion of the wafer, the light scattered from the edge portion of the wafer may be detected using a second detection channel, which is different from the first detection channel. In addition, the first and second detection channels may include different types of detectors. The detectors of the first and second detection channels may be different to account for the different types of scattering that will occur from the center portion and the edge portion of the wafer. In particular, at the edge of the wafer (about 3 mm inward from the outer edge), the detection scheme may be switched automatically to a more "robust" detection scheme such that the excess light scattered from the bevel and the outer edge of the wafer may be handled or disregarded while preserving the scattered light from defects. Since different detection channels may be used to detect defects in different portions of the wafer, the inspection system may have different defect detection thresholds in different portions of the wafer. For example, as shown in FIG. 7, the non-segmented detection channel, which may be used to inspect a center portion of the wafer, may be capable of detecting defects having a size less than 0.2 µm. However, the segmented detection channel, which may be used to inspect an edge portion of the wafer, may be capable of detecting defects having a size less than 0.4 µm.

For an unpatterned wafer, light scattered from the center portion of the back side or the front side of the wafer will not contain Fourier components or other strong scattering components since the center portion of the wafer does not contain any patterned features. However, the edge portion of an unpatterned wafer (and patterned wafers as well) will contain strong scattering components from edge features in the edge portion of the wafer. For example, the bevel in the edge portion may produce strong scattering components that would saturate a non-segmented detector much like the scattered light from patterned features on a wafer would. In this manner, a non-segmented detector may not yield useful signals during scanning of the edge portion of the wafer. In most wafer inspection systems, light scattered from the edge portion of the wafer is blocked from reaching all of the detectors since it is not useful for defect detection.

However, the second detection channel may be configured to separately detect different portions of the light scattered from the edge portion. For example, the second detection channel may include a segmented detector such as detectors 42 and 50 shown in FIG. 3, which may be multi-anode PMTs in one embodiment. Alternatively, detectors 42 and 50 may include an array of photosensitive elements such as photodiodes, which may be arranged as a one-dimensional or two-dimensional array. In addition, detectors 42 and 50 may be array detectors such as charge-coupled device (CCD) cameras or time delay integration (TDI) cameras. Other examples of array detectors include CMOS photodiodes or photogate cameras.

When a segmented detector is used to detect scattered light from the edge portion of the wafer, some segments of the detector may become saturated due to the light scattered from edge features in the edge portion of the wafer. If the segmented detector contains an adequate number of segments (which may be determined as described above), at least some of the segments may detect scattered light that does not contain scattered light from the edge features. Therefore, the output signals generated from the non-saturated segments may be useful for defect detection in the edge portion of the wafer. In addition, light scattered from edge features of the wafer may be separated from other light scattered from the edge portion. In one example, the useful output signals may be separated from the non-useful signals using Fourier filtering, which may be performed as described above. In addition, Fourier filtering may be performed optically (e.g., using a spatial filter) or electronically (e.g., using an appropriate algorithm). In such an embodiment, lens 34 and/or ellipsoidal mirror 44 preferably provide a Fourier plane suitable for Fourier filtering of the light scattered from the edge portion.

In another embodiment, the computer may perform thresholding of the output signals. For example, thresholding may include comparing the signals to a first threshold. This comparison may be used to identify signals or data that contain scattering from edge features on the wafer. If the signals are greater than the first threshold, the signals may be identified as containing such scattering and may be discarded or otherwise not used for defect detection. Thresholding may also include comparing the signals to a second threshold. This comparison may be used to identify signals that contain background scatter or other noise. For example, if the signals are less than the second threshold, these signals may be identified as containing background scatter or noise and may also discarded or otherwise not used for defect detection. The signals that are both below the first threshold and above the second threshold may then be further analyzed for defect detection.

Alternatively, output signals from saturated segments of the detector may be identified and separated from useful output signals using azimuthal filtering. Azimuthal filtering generally refers to the identification and rejection of scatter from features on the specimen such as Manhattan geometry (straight line geometry parallel to rectangular die edges), which changes as the azimuthal angle between the scanned beam and a lateral edge of the features changes. For example, azimuthal filtering of the data or the signals may be performed by the processor using the thresholding technique described above. In such an embodiment, the first threshold may be selected such that comparing the signals or data to the first threshold will identify and eliminate signals from edge features. In another embodiment, the processor may be configured to perform Fourier filtering as described above. Therefore, the system may be configured for "automatic" saturation suppression from an array of photosensitive elements, which makes this detection scheme more robust to saturation while preserving the sensitivity to localized defects like particles, scratches, etc.

In some embodiments, the system illustrated in FIG. 3 may include shutters 58 and 60. Shutter 58 may be configured such that it can be moved in front of detector 40 during scanning of the edge portion. This position of shutter 58 is shown in FIG. 3. Shutter 60 may be configured such that it can be moved in front of detector 46 during scanning of the edge portion. This position of shutter 60 is also shown in FIG. 3. The shutters may be moved in front of the non-segmented detectors during scanning of the edge portion to prevent light scattered from the edge portion from reaching the detectors. In this manner, light strongly scattered from edge features cannot reach the detectors. Therefore, damage which may be caused to the non-segmented detectors by this relatively high intensity light may be prevented. During scanning of the center portion of the wafer, the shutters may be moved out of position in front of the non-segmented detectors in the directions indicated in FIG. 3. The shutters may include any suitable shutters known in the art.

The above-described method is useful for wafer inspection of any wafer surface that has a center portion which does not contain patterned features. In addition, the edge portion on either side of any wafer (patterned or unpatterned) will exhibit the above-described strong scattering from edge features. Therefore, the above-described method will be particularly useful for inspection of the front side of unpatterned wafers, the back side of unpatterned wafers, and the back side of patterned wafers.

Figure 4:
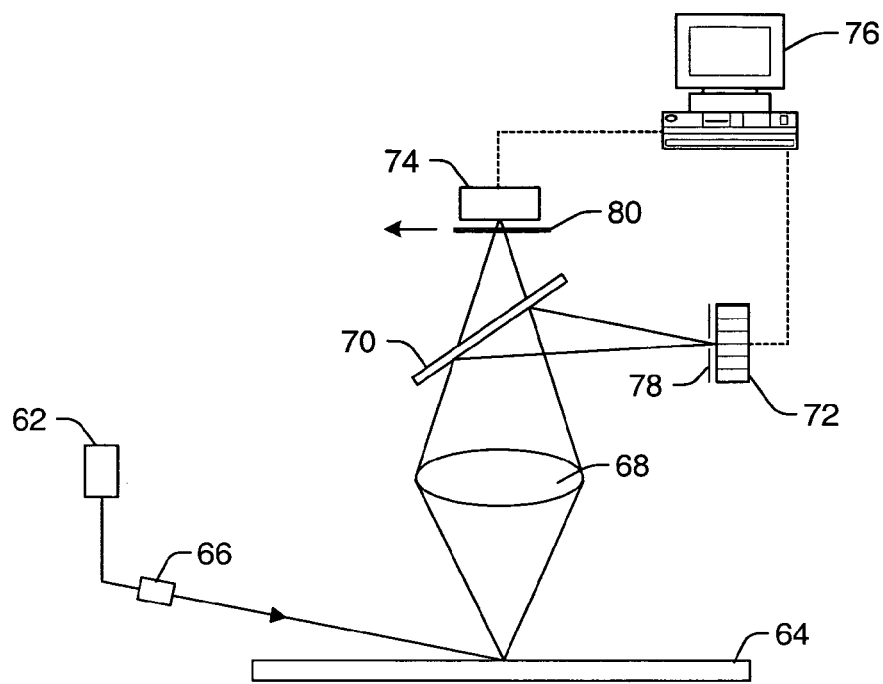

FIG. 4 illustrates another system that may be used to perform the inspection methods described herein. This system includes light source 62. Light source 62 may include, for example, a laser, a diode laser, a helium neon laser, an argon laser, a solid state laser, a frequency doubled YAG laser, a xenon arc lamp, a gas discharging lamp, or an incandescent lamp. The light source may be configured to emit near monochromatic light or broadband light. In addition, the light source may be configured to emit ultraviolet light, visible light, and/or infrared light. Furthermore, the light source may be configured to emit light of various polarizations. The light directed to wafer 64 may also be coherent or incoherent, but coherent monochromatic illumination may be preferred if the system is to filter out signals from pattern features or edge features using Fourier filtering as described herein. The system may also include a number of other components, which are not shown in FIG. 4, such as a beam expander, folding mirrors, focusing lenses, cylindrical lenses, beam splitters, spectral filters, polarizing filters, polarizers, and waveplates.

The system also includes deflector 66. Deflector 66 may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the wafer. In some embodiments, the deflector may scan the light beam over the wafer at an approximately constant scanning speed. In addition, the deflector may be configured to direct light from the light source to a center portion and an edge portion of the wafer in a single scan.

As shown in FIG. 4, the light source and the deflector may be configured to direct the beam of light to the wafer at an oblique angle of incidence. However, this system may also be configured to direct the beam of light to the wafer at a normal angle of incidence. In such an embodiment, the system may not include the deflector since the normal incidence beam of light may be scanned over the wafer by relative motion of the optics with respect to the wafer and/or by relative motion of the wafer with respect to the optics. This system may also be configured to direct multiple beams of light to the wafer such as an oblique incidence beam of light and a normal incidence beam of light.

The system may include a single collection channel, which may be used to collect light scattered from the center and edge portions of the wafer. For example, light scattered from the wafer may be collected by lens 68, which may be a lens or a compound lens. Alternatively, lens 68 may be replaced by a reflective or partially reflective optical component such as a mirror. Lens 68 may be configured to collect light scattered from the wafer over a range of azimuthal angles and a range of polar angles. As used herein, the term "polar angle" is defined as the angle at which light is scattered from the wafer as measured from normal to the surface of the wafer. As used herein, the term "azimuthal angle" is defined as the angle at which light is scattered from the wafer as measured from the plane of incidence. Therefore, lens 68 collects light scattered from the wafer across a two-dimensional space.

Beamsplitter 70 may be configured to direct a portion of the light collected by lens 68 to segmented detector 72. Segmented detector 72 may include any of the segmented detectors described above. In addition, because lens 68 collects the scattered light over a range of azimuthal angles and a range of polar angles, segmented detector 72 may be configured to separately detect different portions of the light collected by lens 68 such that azimuthal and polar angular information about the different portions of the light is preserved. For example, the system may include a plurality of fibers (not shown), which may be configured to separately convey the different portions of the light to the detector as described above. In this embodiment, however, the fibers may be arranged in a two-dimensional array such as a rectangular array instead of one or more rings. In addition, beamsplitter 70 may be configured to allow the other portion of the light collected by lens 68 to impinge upon non-segmented detector 74. Non-segmented detector 74 may include any of the non-segmented detectors described above. In this manner, the two different detectors form different detection channels for the system.

As described above, the position of the incident light on the wafer may be monitored during the single scan. In addition, during scanning of the center portion of the wafer (i.e., the front side or the back side of an unpatterned wafer or the back side of a patterned wafer), the light scattered from the center portion may be detected using a first of the detection channels (e.g., non-segmented detector 74). For example, as described above, light scattered from wafer surfaces that do not contain patterned features or other features can be detected by a non-segmented detector that can produce output signals that are useful for defect detection. Therefore, output signals produced by non-segmented detector 74 may be used by computer 76 to detect defects in the center portion of the wafer.

However, during scanning of the edge portion of the wafer (e.g., the edge portion of any side of a patterned or unpatterned wafer), the light scattered from the edge portion may be detected using the second of the detection channels (e.g., segmented detector 72). The second detection channel is configured to separately detect different portions of the light scattered from the edge portion. In this manner, if any of the segments of the detector are saturated (or otherwise produce non-useful signals) due to scattering from edge features, output signals from other non-saturated segments of the detector may be used to detect defects in the edge portion of the wafer. In addition, light scattered from edge features of the wafer may be separated from other light scattered from the edge portion as described above using, for example, Fourier filtering, thresholding, or azimuthal filtering. In one embodiment, lens 68 may provide Fourier plane 78 suitable for Fourier filtering of the light scattered from the edge portion.

The system illustrated in FIG. 4 may also include shutter 80. Shutter 80 may be placed in front of non-segmented detector 74 during scanning of the edge portion of the wafer. In this manner, the light scattered from the edge portion may be substantially prevented from reaching the non-segmented detector of the first detection channel. The shutter may be moved out of position in front of the non-segmented detector during scanning of the center portion of the wafer.

Figure 5:
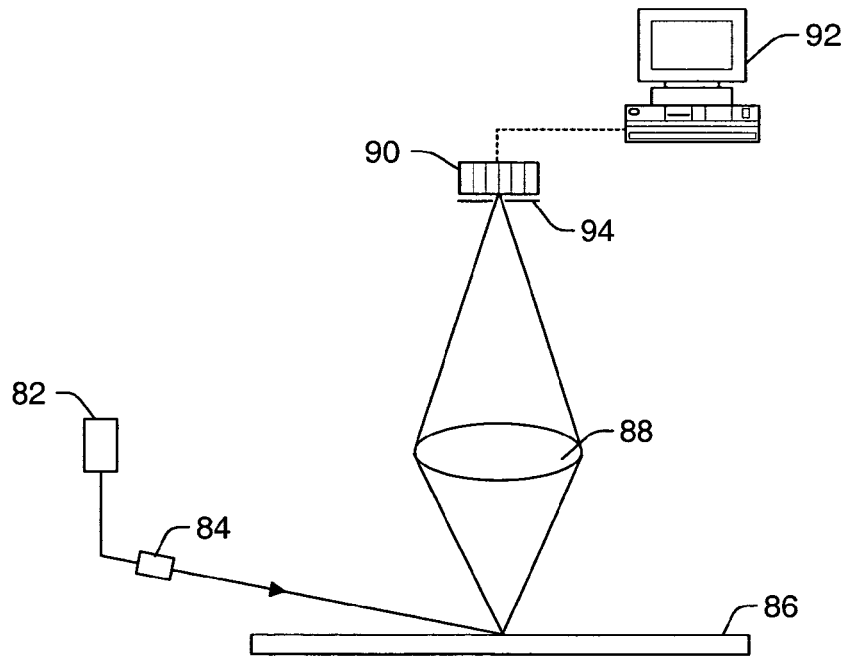

FIG. 5 illustrates another system that may be used to perform a method for inspecting an entire surface of a wafer, including a center portion of the wafer and an edge portion of the wafer, in a single scan. This system includes light source 82 and deflector 84, which may be configured as described above. The light source and the deflector may be configured to direct light to substantially an entire surface of wafer 86 in a single scan. This system also includes lens 88, which may be a lens or a compound lens. Lens 88 may be configured to collect light scattered from the center portion and the edge portion of the wafer. Lens 88 may be further configured as described above. Alternatively, lens 88 may be replaced with a reflective or partially reflective optical component such as a mirror.

Light collected by the lens may be detected by detector 90. This system is different than the others described herein, in that it includes only one detector or detection channel instead or two or more detection channels. However, this system may also be used to detect defects in the center portion and the edge portion of the wafer. For example, the detector may be a segmented detector. In this manner, the detector may separately detect different portions of the light scattered from the wafer and generate individual output signals representative of the different portions of light. In addition, the lens and the detector may be configured to preserve the azimuthal or polar and azimuthal characteristics of the scattered light. This system may also include a plurality of optical fibers (not shown), which may be configured to convey the collected light to the segmented detector. The optical fibers may be configured as described above.

For portions of the wafer that do not contain patterned features or edge features, the scattered light will not contain Fourier components or other scattering components from these features. Therefore, all of the individual output signals generated by the segmented detector may be used to detect defects in unpatterned or feature-less portions of the wafer. As such, the method may include combining the individual output signals generated at the same measurement spot during scanning of the center portion of the wafer when the surface of the wafer being inspected is the front side or the back side of an unpatterned wafer or the back side of a patterned wafer. In addition, the method may include detecting defects in the center portion of the wafer using the combined output signals, which may be performed by computer 92.

For portions of the wafer that do contain patterned features or edge features, the scattered light may contain Fourier components or other strong scattering components from these features. Therefore, some of the individual output signals generated by the segmented detector may be useless for detecting defects in these portions of the wafer. However, other individual output signals that do not contain such scattering components may provide useful signals for defect detection. Therefore, the individual output signals may be used to detect defects in the edge portion of the wafer, which may be performed by computer 92. The individual output signals that are used for defect detection may include only those signals that do not contain Fourier components or other intense scattered light from patterned features or edge features. The individual output signals that can be used for defect detection may be separated from other individual output signals by Fourier filtering, thresholding, or azimuthal filtering, which may be performed as described above. In addition, lens 88 may be configured to provide Fourier plane 94 suitable for Fourier filtering of the light scattered from the wafer.

Each of the above described systems may also be used for inspection of only the edge portion of a wafer. For example, each of the above systems may be used to scan the edge portion of a wafer with light. In addition, the light scattered from the edge portion may be collected with a collector. In some embodiments, the collector may provide a Fourier plane suitable for Fourier filtering of the light scattered from the edge portion. Separately detecting different portions of light scattered from the edge portion may also be performed as described above. The light scattered from edge features in the edge portion may also be separated from other light scattered from the edge portion as described above. Furthermore, defects in the edge portion of the wafer may be detected using the other scattered light.

The systems illustrated in FIGS. 3–5 may be used to inspect an entire front side of an unpatterned wafer, an entire back side of an unpatterned wafer, and an entire back side of a patterned wafer according to the methods described above. In another embodiment, each of the above described systems may also be used to perform a method for inspecting an entire front side of a patterned wafer. For example, the center portion of a patterned wafer may include patterned features that may have any shape (i.e., lines, trenches, contact holes, or vias), period, and orientation known in the art. In some instances, the patterned features may also include non-periodic features. Furthermore, the center portion of the patterned wafer may include other features such as Manhattan geometry. In contrast, the edge portion of a patterned wafer may include edge features such as a bevel and an outer edge. Therefore, the scattering patterns produced by features in the center portion of the wafer may be substantially different that the scattering patterns produced by features in the edge portion of the wafer.

In one embodiment, therefore, different methods may be used to separate light scattered from features on the wafer from other scattered light in the center portion and in the edge portion of the wafer. For example, one Fourier filtering algorithm may be used to eliminate light scattered from features in the center portion of the wafer, and a different Fourier filtering algorithm may be used to eliminate light scattered from features in the edge portion of the wafer. In a similar manner, different thresholding and azimuthal filtering methods or algorithms may be used to identify light scattered from features in the center portion of the wafer and to identify light scattered from features in the edge portion of the wafer. In another example, Fourier filtering may be used to separate light scattered from features in the center portion of the wafer from other light scattered from the center portion of the wafer, while azimuthal filtering may be used to separate light scattered from edge features in the edge portion of the wafer from other light scattered from the edge portion of the wafer. Therefore, the systems and methods described herein may be used to inspect any entire surface of any wafer, patterned or unpatterned.

In another embodiment, different areas of the center portion of a wafer may be inspected using different detection channels and/or different detection methods. For example, the center portion of a front side surface of a patterned wafer may include areas which are densely populated by patterned features and areas which are devoid of patterned features. In this example, a segmented detection channel may be used to inspect the densely populated areas of the center portion while a non-segmented detection channel may be used to inspect the areas devoid of patterned features. In a different example, the center portion of the front side surface of a patterned wafer may include areas that contain periodic patterned features and areas that include non-periodic patterned features. In such an example, a Fourier filtering algorithm may be used to detect defects in the areas that contain periodic patterned features, and a thresholding algorithm or azimuthal filtering may be used to detect defects in the areas that contain the non-periodic patterned features. In yet another such example, different Fourier filtering algorithms may be used in the periodic patterned feature areas and in the non-periodic patterned feature areas.

Additional inspection systems that may be used to perform the methods described herein are illustrated in U.S. patent application Ser. No. 10/456,203 entitled "Systems for Inspection of Patterned or Unpatterned Wafers and Other Specimen" by Bevis et al. filed Jun. 6, 2003, which is incorporated by reference as if fully set forth herein. The inspection systems described herein may be further configured as described in this patent application.

Figure 6:
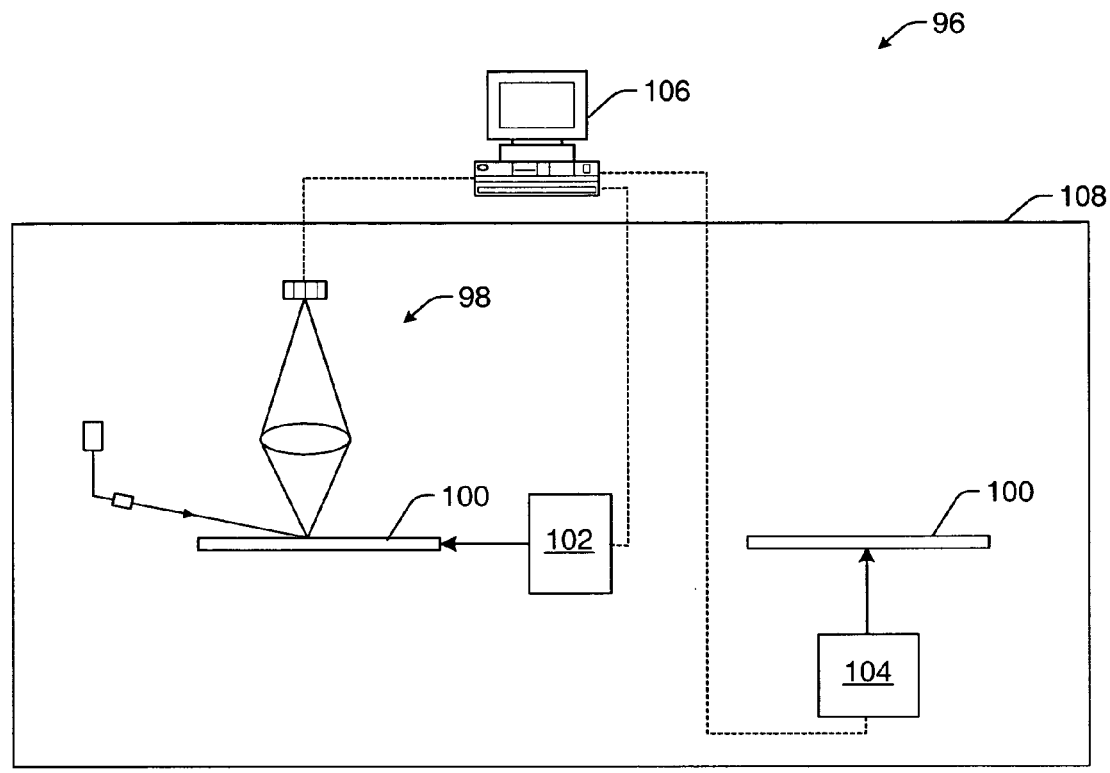

In an additional embodiment, any of the methods described herein may include inspecting substantially the entire front side of a wafer, inspecting substantially the entire back side of the wafer, and inspecting an outer edge of the wafer while the wafer is disposed in a single tool. In this manner, the methods may include inspecting each entire surface of the wafer in a single tool. For example, FIG. 6 illustrates one tool that may be used to perform such a method. As shown in FIG. 6, tool 96 includes inspection system 98. Inspection system 98 is configured as described and illustrated in FIG. 5. However, it is to be understood that this inspection system may be configured as described and illustrated in FIGS. 3 and 4 as well. Inspection system 98 is configured to inspect substantially an entire surface of wafer 100. In some embodiments, the entire surface of the wafer inspected by inspection system 98 may be the entire front side surface of the wafer. In other embodiments, the entire surface of the wafer inspected by inspection system 98 may be the entire back side surface of the wafer.

Tool 96 may also include edge inspection system 102. Edge inspection system 102 may be configured to inspect only the outer edge of the wafer. One example of such an edge inspection system is the EdgeScan system, which is commercially available from Raytex Corporation, Tokyo, Japan. The EdgeScan system uses a very advanced laser and dual-camera system. The laser system delivers a broad band of structured light to the wafer edge, including both top and bottom bevels. Any scattered light caused by defects is captured by two separate high-resolution sensor array cameras. Edge inspection system 102 may be configured to inspect the outer edge of the wafer while inspection system 98 is inspecting an entire front side surface or an entire back side surface of the wafer. In one such embodiment, edge inspection system 102 and inspection system 98 may share a common stage. Alternatively, the edge inspection system may be configured to inspect the outer edge of the wafer before or after inspection system 98 inspects substantially an entire front or back side surface of the wafer.

Tool 96 may also include inspection system 104. Inspection system 104 may be configured to inspect substantially an entire surface of the wafer opposite that which is inspected by inspection system 98. For example, inspection system 98 may be configured to inspect substantially the entire front side surface of the wafer, and inspection system 104 may be configured to inspect substantially the entire back side surface of the wafer. In some embodiments, inspection system 104 may be configured as one of the systems illustrated in FIGS. 3–5 described herein. In another embodiment, inspection system 104 may be configured as described in U.S. Pat. No. 6,204,917 to Smedt and U.S. Pat. No. 6,559,938 to Smedt, which are incorporated by reference as if fully set forth herein. In one embodiment, inspection systems 98 and 104 may be configured to inspect opposite sides of the wafer while the wafer is disposed on different stages (not shown). For example, if the stage that supports the wafer while inspection system 98 inspects the front side of the wafer contacts the back side of the wafer, then the wafer may be moved to a different stage which does not support the wafer through back side contact such that substantially the entire back side surface of the wafer may be inspected by inspection system 104.

In another embodiment, the wafer may be held in place by an edge handling mechanism. In this embodiment, inspection system 98 may be configured to inspect substantially the entire front side or back side of the wafer while inspection system 104 inspects substantially the entire opposite side of the wafer. In such an embodiment, the position of inspection systems 98 and 104 would not be laterally offset from one another. Instead, inspection system 98 would be arranged directly opposite the wafer from inspection system 104. Edge inspection system 102 may be configured to inspect the outer edge of the wafer while inspection system 104 is inspecting an entire front side surface or an entire back side surface of the wafer. In such an embodiment, edge inspection system 102 and inspection system 104 may share a common stage. Alternatively, the edge inspection system may be configured to inspect the outer edge of the wafer before or after inspection system 104 inspects substantially an entire front or back side surface of the wafer.

As shown in FIG. 6, the system may also include computer 106. Computer 106 may be coupled to inspection systems 98, 102, and 104 by a transmission medium as shown by the dotted lines in FIG. 6. In this manner, the three inspection systems may be configured to share a common computer. Computer 106 may also be configured to receive output signals generated by the various inspection systems. In addition, computer 106 may be configured to detect defects on each of the inspected surfaces using the output signals. The computer may also be configured to perform any other analysis of the output signals. For example, the computer may be configured to perform methods for correlating backside and frontside defects detected on a specimen and classification of backside defects. Examples of such methods are illustrated in U.S. Patent Application Ser. No. 60/416,136 to Haller et al., filed Oct. 4, 2002, which is incorporated by reference as if fully set forth herein. As further shown in FIG. 6, computer 106 may be disposed outside of housing 108 in which inspection systems 98, 102, and 104 are disposed. However, computer 106 may also be disposed inside of housing 108. In addition to sharing a common computer, in some embodiments, inspection systems 98, 102, and 104 may share a common handler, a common power source, and/or a common environment.

In another embodiment, any of the inspection systems described herein may be configured to inspect more than one surface of the wafer. For example, the inspection systems may includes a mechanical device that may be configured to change the surface of the wafer that is inspected by the system. For example, the inspection system may include a Back Side Inspection Module (BSIM), which is commercially available from KLA-Tencor, as part of the SP1 laser-based wafer inspection tool. The BSIM enables non-destructive front side and back side inspection of a wafer through wafer edge handling and a "flipping" mechanism. Therefore, the wafer handling is designed such that the front side of the wafer is not damaged during inspection of the back side of the wafer. In this manner, back side inspection of both product and non-product wafers may be performed by the inspection system. In one embodiment, therefore, tool 96 may include inspection system 98 and edge inspection system 102 but not inspection system 104 since inspection system 98 may be used to inspect substantially entire opposite sides of the wafer.

Further modifications and alternative embodiments of various aspects of the invention may be apparent to those skilled in the art in view of this description. For example, methods and systems for inspecting an entire wafer surface using multiple channels are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for inspecting a wafer, comprising:
   directing light to a center portion and an edge portion of the wafer in a single scan;

detecting light scattered from the center portion using a first detection channel; and detecting light scattered from the edge portion using a second detection channel, wherein the first and second detection channels comprise different types of detectors.

2. The method of claim 1, wherein the edge portion extends about 3 mm inward from an outer edge of the wafer.

3. The method of claim 1, wherein the center portion and the edge portion have a combined surface area approximately equal to an entire surface area of a front side of the wafer.

4. The method of claim 1, wherein the center portion and the edge portion have a combined surface area approximately equal to an entire surface area of a back side of the wafer.

5. The method of claim 1, wherein the first detection channel further comprises a photo-multiplier tube.

6. The method of claim 1, wherein the first detection channel is configured to generate a single output signal at each measurement spot.

7. The method of claim 1, wherein the second detection channel further comprises a segmented detector.

8. The method of claim 1, wherein the second detection channel further comprises an array of photosensitive elements.

9. The method of claim 1, wherein the second detection channel is configured to separately detect different portions of the light scattered from the edge portion, the method further comprising separating light scattered from edge features of the wafer from other light scattered from the edge portion.

10. The method of claim 1, further comprising collecting the light scattered from the center and edge portions of the wafer with a single collection channel and directing the light collected by the single collection channel to the first and second detection channels.

11. The method of claim 1, further comprising collecting the light scattered from the edge portion of the wafer with a collector, wherein the collector provides a Fourier plane suitable for Fourier filtering of the light scattered from the edge portion.

12. The method of claim 1, further comprising substantially preventing the light scattered from the edge portion from reaching a detector of the first detection channel.

13. The method of claim 1, wherein the center and edge portions are located on a front side of the wafer, the method further comprising inspecting the front side of the wafer, substantially an entire backside of the wafer, and an outer edge of the wafer while the wafer is disposed in a single tool.

14. A method for inspecting a wafer, comprising:

directing light to a center portion and an edge portion of the wafer in a single scan, wherein the edge portion extends about 3 mm inward from an outer edge of the wafer;

detecting light scattered from the center portion using a first detection channel;

separately detecting different portions of light scattered from the edge portion using a second detection channel, wherein the first and second detection channels comprise different types of detectors;

separating light scattered from edge features in the edge portion from other light scattered from the edge portion; and detecting defects in the edge portion of the wafer using the other light.

15. The method of claim 14, further comprising collecting the light scattered from the edge portion with a collector, wherein the collector provides a Fourier plane suitable for Fourier filtering of the light scattered from the edge portion.

16. A method for inspecting a wafer, comprising:

directing light to substantially an entire surface of the wafer in a single scan, wherein the entire surface comprises a center portion and an edge portion;

separately detecting different portions of light scattered from the wafer to generate individual output signals representative of the different portions of light;

combining the individual output signals generated at the same measurement spots during said separately detecting at the center portion of the wafer;

detecting defects in the center portion of the wafer using the combined output signals; and detecting defects in the edge portion of the wafer using the individual output signals.

17. The method of claim 16, wherein the wafer is an unpatterned wafer.

18. The method of claim 16, wherein the entire surface of the wafer comprises a front side surface of the wafer.

19. The method of claim 16, wherein the entire surface of the wafer comprises a back side surface of the wafer.

* * * * *